US006730045B2

(12) United States Patent
Finer

(10) Patent No.: US 6,730,045 B2
(45) Date of Patent: May 4, 2004

(54) BIOPSY NEEDLE FOR CONTINUOUS SAMPLE REMOVAL

(76) Inventor: Richard Finer, 551 Alta Vista Dr., Sierra Madre, CA (US) 91024-1412

( * ) Notice: Subject to any disclaimer, the term of this patent is extended or adjusted under 35 U.S.C. 154(b) by 16 days.

(21) Appl. No.: 09/887,196

(22) Filed: Jun. 22, 2001

(65) Prior Publication Data

US 2002/0198467 A1 Dec. 26, 2002

(51) Int. Cl.⁷ ............................ A61B 5/00; B65D 81/00
(52) U.S. Cl. ................................................ 600/573
(58) Field of Search ........................... 606/180, 171; 600/564; 200/259; 128/754, 305; 604/165

(56) References Cited

U.S. PATENT DOCUMENTS

| 4,850,354 A | * | 7/1989 | McGurk-Burleson et al. | 128/305 |
|---|---|---|---|---|
| 5,224,488 A | | 7/1993 | Neuffer | |
| 5,538,009 A | * | 7/1996 | Byrne et al. | 128/754 |
| 5,571,091 A | * | 11/1996 | Davis et al. | 604/165 |
| 5,720,490 A | | 2/1998 | Chang | |
| 5,720,760 A | * | 2/1998 | Becker et al. | 606/180 |
| 5,722,985 A | * | 3/1998 | Pettus | 606/180 |
| 5,769,086 A | | 6/1998 | Ritchart et al. | |
| 5,823,970 A | | 10/1998 | Terwilliger | |
| 5,916,229 A | * | 6/1999 | Evans | 606/171 |
| 5,944,673 A | | 8/1999 | Gregoire et al. | |
| 5,961,534 A | | 10/1999 | Banik et al. | |

OTHER PUBLICATIONS

Automated Biopsy Systems Flyer.

* cited by examiner

Primary Examiner—Henry Bennett
Assistant Examiner—Sabrina Dagostino
(74) Attorney, Agent, or Firm—Vierra Magen Marcus Harmon & DeNiro LLP

(57) ABSTRACT

Described herein is a biopsy needle comprising a hollow outer tube at the end of which is a rectangular opening having sharpened edges. In preferred embodiments, the needle has one lumen formed by the needle or two lumens, formed either by a second hollow member positioned within the needle, or a ------- semi-circular tube inserted within the needle. To remove tissue using the needle, one inserts it into a patient's body, applies suction to the single or double lumens and then rotates the needle. Tissue is drawn into the needle lumen for subsequent evaluation by a Pathologist.

43 Claims, 3 Drawing Sheets

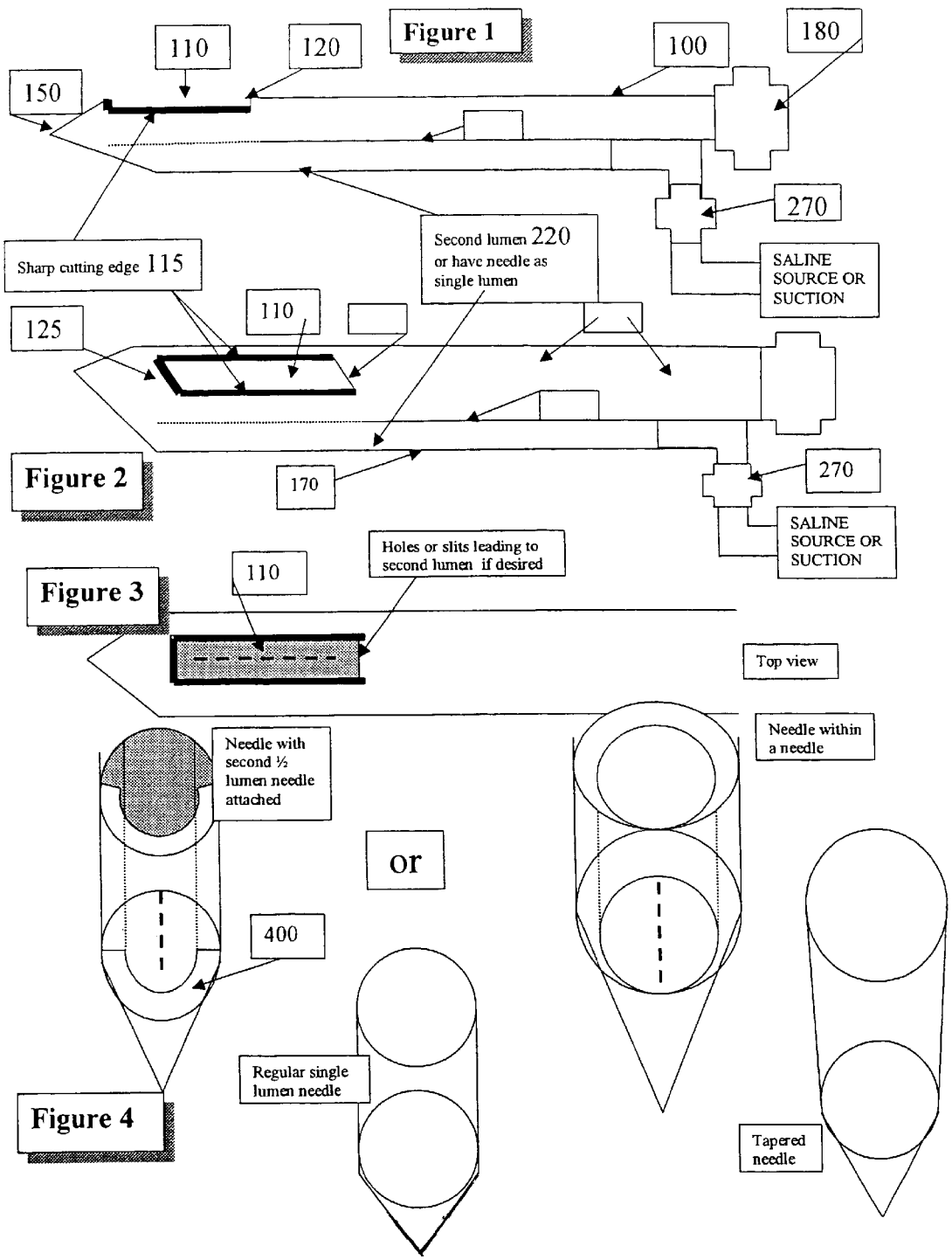

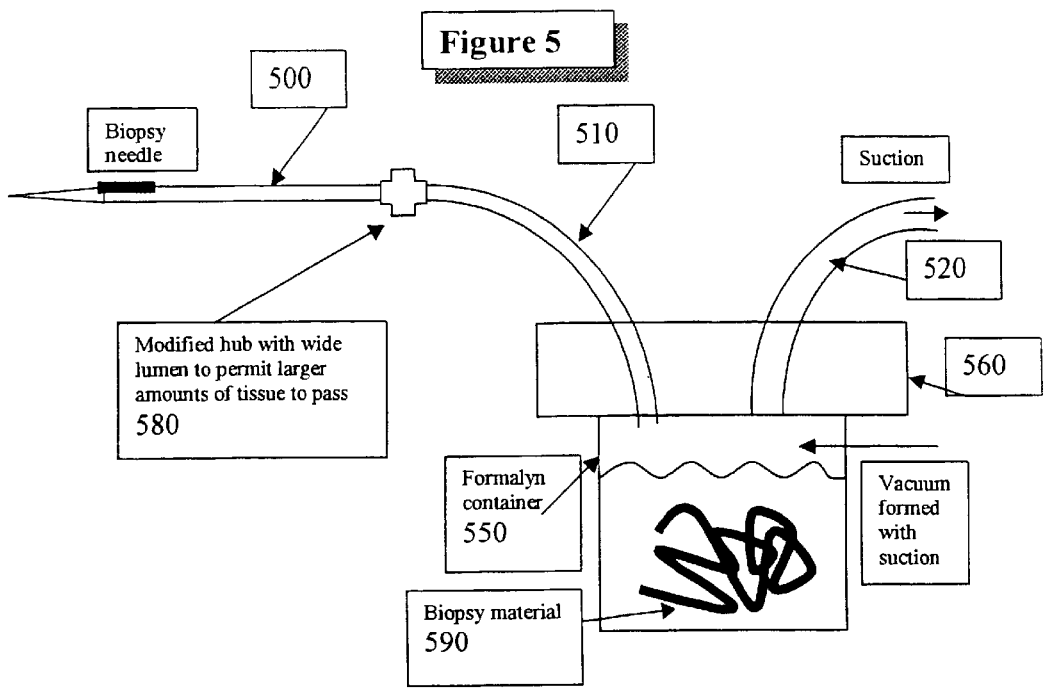
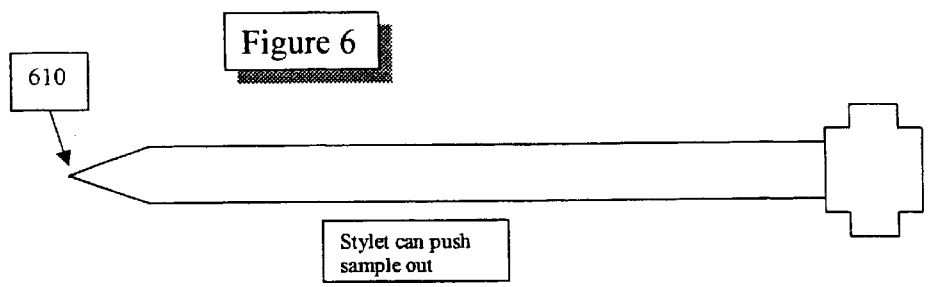
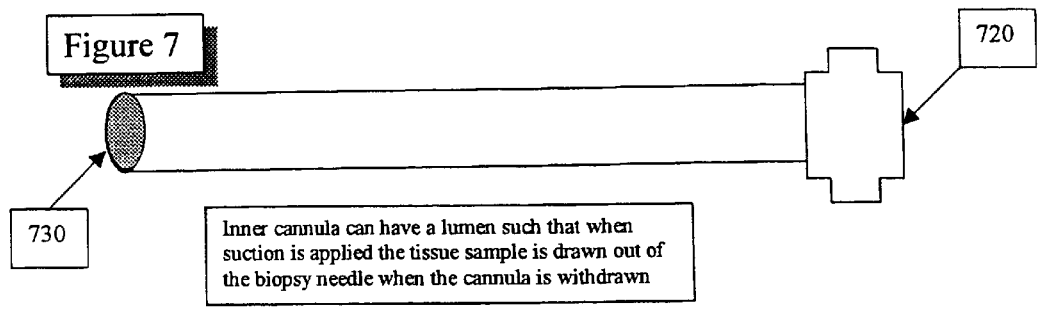

FINER BIOPSY NEEDLE DRAWINGS

810

910

101

116

BIOPSY NEEDLE FOR CONTINUOUS SAMPLE REMOVAL

FIELD OF THE INVENTION

Embodiments of the present invention are directed to a biopsy needle for removal of tissue from a body for examination outside of the body.

BACKGROUND OF THE INVENTION

A biopsy needle is used to obtain a sample of tissue from the body (usually from the human body, but often from the body of a non-human animal, as well) for diagnosis of disease or other examination. The sample obtained should be uniform and substantial enough to permit one to examine its structure and composition. When the sample is used for diagnosing disease, the sample should be representative of the tissue from which the sample is removed. If the sample is obtained with the proper technique and a correct instrument, it will be large and uniform enough to make diagnostically relevant findings from it.

The challenge in biopsy needle design is principally to meet two conflicting goals: 1) provide a needle that is large enough to obtain a sample of sufficient size; and 2) provide a needle that is small enough to minimize trauma to the patient. Minimizing trauma means more than minimizing pain (about which the patient cares a great deal, of course): a smaller incision in the body heals more quickly, bleeds less, minimizes infection, and reduces scarring. Current biopsy design meets these goals with varying degrees of success; many designs meet one goal but at significant expense to the other.

Biopsy needles that tend to be successful (more or less) at withdrawing large samples from a patient but with minimal trauma are almost invariably complex and expensive. They often depend on costly suction equipment and needles (as does the MAMMOTOME®, for example) and/or a complex cutting mechanism. Complexity is undesirable because it increases the time required to learn to use a device, it increases the tendency of a device to fail, and it makes the device more expensive to manufacture.

There is therefore an important need in the art for a device that can remove a sufficient amount of sample with minimal trauma to a patient, and that is simple, easy to use, and inexpensive to manufacture.

SUMMARY OF THE INVENTION

It is an object of the present invention to provide a biopsy needle and biopsy needle device that can obtain a tissue sample of large size. It is a further object of the present invention that this sample is large enough so as to permit one to make diagnostically relevant findings from it. It is a still further object of the invention to provide a biopsy needle and biopsy needle device that obtains such a sample while at the same time minimizing trauma to the patient from whom the sample is obtained.

It is another object of the invention to provide a biopsy needle and biopsy needle device that is uncomplicated, that is easy to use, and that is cheaper to manufacture than are typical biopsy needles.

These and other objects are achieved by the biopsy needle and biopsy device of the invention. In a preferred embodiment of the invention, the biopsy needle comprises a hollow outer tube. At the distal end of the tube are two longer parallel edges and two shorter parallel edges that define a rectangular opening. The edges are preferably at right angles to one another, such that the longer edges are perpendicular to the short edges. The longer edges, and the shorter edge near the distal end, are sharpened to provide a razor-sharp cutting edge; the shorter edge away from the distal end is a standard edge. The hollow outer tube may be straight with the same diameter throughout or tapered towards the distal end.

In a presently preferred method of removing tissue with the biopsy needle of the invention, one inserts it into a patient's body at a desired location and applies negative pressure via a syringe inserted at the proximal end of the needle. One then either rotates the needle or turns it back and forth. Tissue is drawn into the rectangular opening by the negative pressure, is sliced by the sharp cutting edges of the opening as the cutting edges remove tissue, and is then deposited into the lumen of the needle. As long as negative pressure is applied, tissue can be cut and deposited into the lumen throughout the cutting process.

The method and device of the invention permit one to use a needle of limited size to obtain a large amount of tissue—and even remove a tumor completely—from a single, small insertion point. This is a significant advantage over prior art devices for diagnostic procedures, because a smaller caliber needle can be used to obtain a better tissue sample, thus minimizing potential complications and maximizing sample yield. Additionally, in certain therapeutic procedures the needle may remove the lesion completely and eliminate the need for subsequent surgical removal of tissue from the biopsy site. It moreover significantly decreases the chance that the physician performing the biopsy will miss a focus of abnormal tissue, because tissue is removed, as the needle is moved over tissue, at an increasing distance from the insertion point of the needle. This yields a larger and more representative sample of tissue for subsequent pathology evaluation, and avoids the need for multiple biopsy procedures. Limiting the number of biopsy procedures a patient must endure is a significant advantage of the invention, as it decreases both the discomfort and complications that are commonly associated with such procedures. In addition, the simplicity of the device allows one to quickly learn to use it, as well as significantly reduces its manufacturing cost.

BRIEF DESCRIPTION OF THE DRAWINGS

FIG. 1 is a side view of a biopsy device according to the invention having two lumens, wherein the second lumen is attached to a source of liquid, room air, or suction.

FIG. 2 is a perspective view of a the biopsy device shown in FIG. 1.

FIG. 3 is a top view of the biopsy device shown in FIG. 1.

FIG. 4 is a view of the biopsy device of FIG. 1 showing the second lumen of the device.

FIG. 5 shows the biopsy device according to the invention having a single lumen, wherein the device is attached to a source of suction.

FIG. 6 shows a stylet that may be used to push material out of any of the biopsy devices shown in the previous figures.

FIG. 7 shows a cannula that may be inserted in the primary lumen of any of the biopsy devices shown in the previous figures, in order to apply suction to material as it enters the lumen.

DETAILED DESCRIPTION OF THE INVENTION

Figure 8:
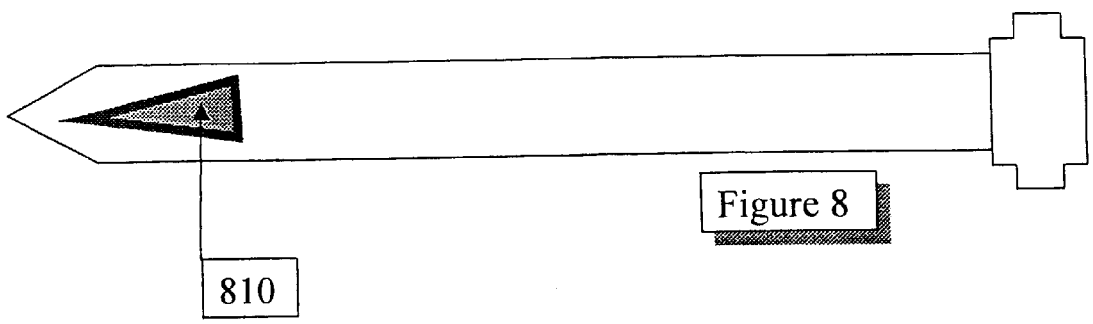
FIG. 8 shows a biopsy device according to the invention, having an opening for cutting in the shape of a triangle.

FIG. 1 is a side view of one embodiment of a biopsy needle according to the present invention. A hollow outer tube 100 has a length between about 40 mm and 250 mm, and preferably between about 50 mm and 200 mm. For biopsies taken from superficial sites, such as near the skin surface, a length of about 50 mm is preferred; for biopsies taken from deeper within the body, a length of about 200 mm is preferred. The outer diameter of the tube is that of a standard biopsy needle of approximately 11 to 22 gauge. The precise diameter and length of the needle depends on the amount of tissue desired to be sampled, the location of the biopsy within the body, and should be readily apparent to one of ordinary skill in the art.

The distal end 150 of the tube may be either closed or open. In the preferred embodiment shown, the diameter of the tube decreases sharply a few millimeters from the distal end of the tube, forming a sharp point that permits one to puncture the tissue into which the needle is to be inserted, or to penetrate the tissue more easily. One may optionally use with this needle another device, such as a trocar or other needle, to penetrate the tissue to the margin of the biopsy site through which the needle of invention is then inserted; but using another device is not necessary. In alternative embodiments, the distal tip of the tube remains open. In such embodiments, the use of another device to puncture the tissue is generally required.

An opening 110 is at the distal end 150 of the tube, formed by two parallel shorter edges 120, and two parallel longer edges 115. The shorter parallel edges 120 have a length of between about 15 to 50% of the diameter of the hollow outer tube. The longer parallel edges 115 are between about 5 mm and 30 mm in length. The longer parallel edges 115 shown in FIG. 1 are illustrated in their preferred embodiment, that is, positioned parallel to the longitudinal axis of the tube, but in alternate embodiments may be positioned at angle anywhere from about 0–45° from this axis. The shorter parallel edges 120 are shown also in their preferred embodiment, positioned perpendicular to the longitudinal axis of the tube. At least one shorter parallel edge is sharpened to provide a razor-sharp cutting edge 125. Preferably both longer parallel edges are razor sharp, as is the shorter parallel edge 125 (see FIG. 2) closest to the distal end 150 of the tube. The proximal aspect of the tube may terminate in any standard biopsy needle hub 180, well known to those of ordinary skill in the art of biopsy needle design. One such hub is shown in U.S. Pat. No. 5,720,760, the entirety of which is incorporated by reference.

FIG. 2 shows a biopsy needle according to the invention from an oblique view. The needle is the same as that illustrated in FIG. 1, but visible is a flat member 200 having a width approximately equal to the inner diameter of the tube and running most of the tube's length. It is positioned parallel to the longitudinal axis of the tube, but closer to the bottom 170 of it. The effect is to divide the body of the tube into a main lumen 210 and a secondary lumen 220. The flat member 200 may be placed at any position in which it is substantially parallel to the longitudinal axis of the tube, so long as it provides sufficient room for material to be collected within the main lumen 210. In a preferred embodiment, the member is placed a distance approximately equal to ¼ the diameter from the bottom 170 of the tube.

The secondary lumen of the hollow outer tube of FIG. 2 departs from the main lumen and main hub (180) and terminates at a secondary hub 270 at the proximal end of the outer tube. The secondary hub 270 may be attached to a source of fluid, such as saline, to a source of suction, or open to room air. Holes are placed along the distal aspect of the flat member 200, directly underneath the rectangular opening 110. The holes permit fluid and/or air to pass between the primary and secondary lumens.

When the secondary hub is attached to a source of fluid or room air, the primary hub 180 may be attached to a source of negative pressure. Delivering negative pressure to the primary lumen causes fluid or room air to be drawn into the secondary lumen; the fluid or air passes through the holes positioned under the rectangular opening 110 and flows into the main lumen, where the fluid or air is drawn out by negative pressure. As tissue is ablated by the sharpened parallel edges of the rectangular opening, the tissue is drawn into the lumen by the negative pressure and travels with the fluid or air as it flows from the distal end to the proximal end of the main lumen. The use of fluid or room air and suction in this manner prevents tissue from accumulating within the main lumen and clogging it; this can be a problem when removing large amounts of tissue, as when one seeks to completely remove a tumor, but is remedied by the use of fluid or air and suction according to the invention. A syringe or any other simple container can be used to provide a suitable source of fluid or just open to the room air.

In an alternative embodiment, negative pressure can be applied to the secondary lumen (as shown in FIG. 1), thereby drawing tissue into the opening for removal. Suction is also applied in this embodiment to a hollow cannula (FIG. 7) positioned in the primary lumen with the distal tip of the cannula positioned just proximal to the biopsy opening. The tissue that is subsequently biopsied inside the primary lumen is then extracted by gradually withdrawing the hollow cannula to which negative pressure is applied while the outer biopsy needle is being rotated. During this extraction, negative pressure is maintained on the secondary lumen to keep tissue within the biopsy opening for ablation.

FIG. 3 shows the needle of the invention from a top view. The opening 110 is shown in its preferred shape of a rectangle, that is, with the longer parallel edges and the shorter parallel edges forming 90° angles. The opening need not be in this shape, however. It may be in the shape of a parallelogram, for example, with the longer parallel edges and shorter parallel edges forming two angles of more than 90°, and two angles less than 90°. In still other embodiments, the opening may be in the shape of an oval, circle, triangle, or any other closed shape having approximately the same area as the rectangular opening previously described.

In the embodiment wherein the opening is a triangle (FIG. 8), the opening 810 is defined by two longer edges and one shorter edge defining a triangular opening. The longer edges meet at a point facing the distal edge; the base of the triangle lies 30 mm away from this point towards the proximal end of the hollow outer tube.

Figure 9:
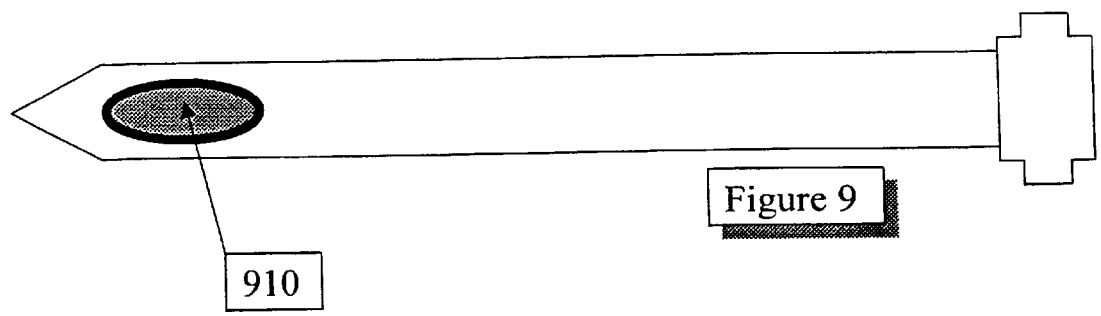
FIG. 9 shows a biopsy device according to the invention, having an opening for cutting in the shape of an ellipse.

In the embodiment wherein the opening is an ellipse (FIG. 9), the opening 910 is defined by an elongated cutting edge sharpened along most of its surface. One focus of the ellipse is about 0.5 mm–20 mm from the second end of the outer tube; the other focus is at least 5 mm further from the second end. The sum of the distance between one focus and a point on the edge, and the other focus and the point, is equal to about 50–150% of the diameter of the tube.

Figure 10:
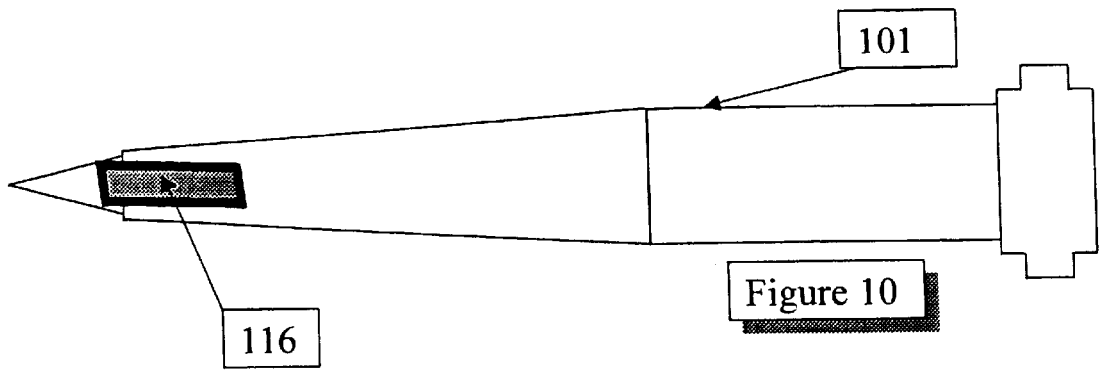
FIG. 10 shows a tapered biopsy device according to the invention, having an opening for cutting in the shape of a parallelogram, and wherein the diameter of the needle begins to steadily decrease at a point at least halfway from the proximal end of the needle.

Any cutting opening—rectangular, triangular, elliptical—may be used with a needle that a substantially constant outer diameter throughout or with a needle that tapers towards the opening. FIG. 10 shows a tapered needle wherein the opening is a parallelogram (116). The outer tube of the needle 101 has a substantially constant diameter for at least half of the proximal end of the tube; at a point at least halfway away from the proximal end, the diameter begins to constantly decrease until 0.0–20 mm from the distal end of the needle.

FIG. 3 further shows the holes placed in the flat member 200 of the needle illustrated in FIG. 1. The holes are present in the portion directly underneath the opening 110 of the needles illustrated in FIGS. 1 and 2.

In a preferred embodiment illustrated in FIG. 4, the secondary lumen is formed by a second semi-circular tube 400 placed within the outer hollow tube. The flat edge of the tube (the edge defined by the base of the semi-circle) forms a boundary that eliminates the need for the flat member shown in FIG. 2. The inside of the semi-circular tube forms the secondary lumen, while the space outside of it forms the main lumen of the outer hollow tube. The semi-circular tube 400 has a diameter less than that of the hollow outer tube, and it is placed preferably along most of the length of the hollow outer tube. Like the flat member, the inner semi-circular tube has holes along its distal end so as to permit the main lumen and secondary lumen to communicate with one another.

The needle is preferably made from surgical stainless steel, but may be made from any material known in the art to be suitable for biopsy needles; the choice of material is not important as long as the material is sufficiently rigid, may be sharpened to provide a fine cutting edge along the parallel edges of the rectangular opening, and has a high resistance to rust and other forms of corrosion.

To use the needle, one inserts it into the body of an animal (preferably a human patient, though the patient need not be a human and the term "animal" as used herein may be a human or non-human animal) at the locus of tissue at which one wishes to obtain a sample. One then applies suction to the needle. One may use suction for at least two purposes: to draw tissue close to the cutting edge, helping to ensure a clean cut; and/or to draw material away from the cutting areas and into the proximal portion of the main lumen, to help prevent blockage. The manner in which one applies suction depends on whether one uses a single-lumen or a double-lumen needle.

When using a single-lumen needle, one may apply suction by attaching a source of negative pressure such as a syringe with the plunger pulled back or a different source of continuous suction at the proximal end of the needle. The needle is then rotated allowing for ablated tissue to enter the needle and possibly the syringe; or, if continuous suction attachment is utilized, the ablated tissue can be deposited into a container. FIG. 5 illustrates how continuous suction may be applied in this manner.

As shown in FIG. 5, the single-lumen or double lumen biopsy needle 500 according to the invention is attached at its proximal end via hub 580 to a flexible tube 510, which is attached to an air-tight container 550 at its top 560. The hub 580 may have a wider diameter than is typical of standard hubs to accommodate larger samples of tissue passing through. The container is preferably made of plastic, but may be made of any material capable of providing an air-tight chamber. Use of a FORMALYN® container is especially preferred. A second tube 520 is attached at one end to the top 560 of the air-tight container 550 and attached at its other end to a vacuum source (not shown). The vacuum source applies a negative pressure, inducing a negative pressure within the container, and thereby inducing a negative pressure within the lumen of the biopsy needle 500. The negative pressure draws tissue 590 out from the outer and/or inner tube, which is collected in the container 550.

FIG. 6 illustrates a stylet which may be used to push a sample of tissue out from the opening of the biopsy needle onto a holder (such as a slide) for subsequent analysis. The stylet comprises a needle or other tube (whether hollow or not) of small enough gauge to permit one to insert it within the main lumen of the biopsy needle. FIG. 6 shows a stylet wherein the distal end 610 of the stylet narrows to a fine point.

FIG. 7 shows a hollow cannula having a hub 720 at its proximal end and an opening 730 at its distal end. The cannula can be made of any material of which cannulas are customarily made. One can attach a source of negative pressure to the proximal end of the cannula and insert it into the main lumen of the biopsy needle. One can then advance the cannula up to a point near or directly under (but preferably at the proximal end of) the rectangular opening. As one ablates tissue with the needle and applies negative pressure with the cannula, one can gradually withdraw the cannula, thereby moving material along with cannula into the proximal end of the main lumen. This provides additional room for a continuous sheet of tissue to be ablated and deposited in the lumen until the cannula is completely removed. This may allow one to completely remove a mass of tissue (which may be a neoplasm or nodule) with a single percutaneous procedure. One may apply suction with the cannula of FIG. 7 instead of, or in addition to, using the suction device of FIG. 5.

Use of a two-lumen needle (FIGS. 1–4) is preferred for removing large samples of tissue, because such samples pose a greater risk of occluding the lumen of the needle. Two lumens need not be present, however, to successfully use the biopsy needle of the invention. The single-lumen needle may also be used, with or without suction, for removing samples of tissue of all sizes. A two-lumen needle, however, permits one to use fluid or air to clear tissue from the main lumen of the needle. The use of suction in a this manner is as previously described, and may be supplemented with the use of the suction cannula illustrated in FIG. 7.

In an alternative embodiment, suction can be applied to the secondary lumen (as shown in FIG. 1), thereby drawing tissue into the opening for removal. Suction is also applied in this embodiment to the hollow cannula (shown in FIG. 7) positioned in the primary lumen with the distal tip positioned just proximal to the biopsy opening. The tissue that is subsequently biopsied inside the primary lumen is then extracted by gradually withdrawing the hollow cannula to which negative pressure is applied while the outer biopsy needle is being rotated. During this extraction, negative pressure is maintained on the secondary lumen to keep tissue within the biopsy opening for ablation.

After one inserts the needle and applies suction, one either turns the needle back and forth, or, preferably, rotates the needle. As the needle turns or rotates, the razor-sharp edges of the rectangular opening engage tissue, ablating a thin portion of it. The more one turns the needle, the more tissue the needle obtains, permitting one to obtain a large sample from a single insertion point. The amount of tissue ablated is determined in part by the length and width of the opening for the cutting edge; wider openings ablate a thicker portion of tissue. By continuously rotating the needle, one can obtain a continuous sheet of tissue. Suction draws the tissue into the lumen and clears it to make room for more tissue. If applying suction with a cannula, one can withdraw the cannula from the needle, along with the tissue held to cannula with negative pressure, to clear any occlusions in the lumen.

One could also use the biopsy needle to completely remove a neoplasm or any other undesirable growth. To use the biopsy needle for this purpose, one inserts it in the same manner as one inserts the needle for the collection of tissue samples. One then proceeds to rotate the tube until it completely ablates the area of tissue containing the neoplasm to be removed; one may have to move (rather than rotate) the needle itself to change the locus at which it is removing tissue to ensure that the entire tumor is removed. Samples obtained using the method of the invention are submitted to a pathologist for examination. Once the pathologist sees no tumor cells, it may be presumed that the tumor was completely removed from the inside out until normal cells were obtained.

While the description above refers to particular embodiments of the present invention, one may make many modifications to it without departing from the spirit of the teachings set forth herein. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than by the foregoing description.

What is claimed is:

1. A biopsy device for removing tissue from the body of an animal, the device comprising:

an elongated hollow outer tube adapted to receive an inner tube, the hollow outer tube comprising a first end, a second end, and a longitudinal axis, wherein the outer tube has a total length of about 40 mm–250 mm and a diameter of a 11–22 gauge needle;

two substantially parallel longer edges and two substantially parallel shorter edges defining a rectangular opening about 0.5 mm–20 mm from the second end of the outer tube, wherein the longer edges are positioned within 0–45° from the longitudinal axis of the outer tube, have a length of about 5 mm–30 mm, and are sharpened to a cutting edge, and wherein the shorter edges have a length equal to about 15–50% of the diameter of the hollow outer tube, and wherein the shorter edge closer to the second end of the tube is sharpened to a cutting edge; and a hub attached at the first end of the hollow outer tube.

2. The biopsy device of claim 1, wherein the device further comprises a source of negative pressure attached to the first end of the hollow outer tube.

3. The biopsy device of claim 2, wherein the source of negative pressure comprises a sealed container, a first flexible tube having two ends, and a second flexible tube having two ends, wherein one end of the first flexible tube is connected to the first end of the hollow outer tube and the other end of the first tube is connected to the container, and wherein one end of the second flexible tube is connected to the container and the other end is connected to a device that draws air from the container.

4. The biopsy device of claim 1, wherein the outer tube further comprises an elongated member positioned within the hollow outer tube substantially parallel to its longitudinal axis, so as to separate the tube into a first lumen and a second lumen.

5. The biopsy device of claim 4, wherein the device further comprises a source of negative pressure attached to the second lumen at its first end.

6. The biopsy device of claim 5, wherein the source of negative pressure comprises a sealed container, a first flexible tube having two ends, and a second flexible tube having two ends, wherein one end of the first flexible tube is connected to the first end of the hollow outer tube and the other end of the first tube is connected to the container, and wherein one end of the second flexible tube is connected to the container and the other end is connected to a device that draws air from the container.

7. The biopsy device of claim 1, wherein the device further comprises an elongated hollow inner semi-circular tube having a flat base, a radius that is less than half of the diameter of the hollow outer tube, and when inserted into the hollow outer tube creates two lumens;

wherein the first lumen is defined by the space between the flat base and the inner surface of the outer hollow tube; and wherein the second lumen is defined by the space inside the inner semi-circular tube; and wherein the flat base has holes along its surface in an area under the rectangular opening, to permit the first lumen to communicate with the second lumen.

8. The biopsy device of claim 7, wherein the hollow inner semi-circular tube further comprises a hub attached to the first end of the semi-circular tube.

9. The biopsy device of claim 8, wherein the device further comprises a source of negative pressure attached to the hub of the semi-circular tube.

10. The biopsy device of claim 9, wherein the source of negative pressure comprises a sealed container, a first flexible tube having two ends, and a second flexible tube having two ends, wherein one end of the first flexible tube is connected to the first end of the hollow outer tube and the other end of the first tube is connected to the container, and wherein one end of the second flexible tube is connected to the container and the other end is connected to a device that draws air from the container.

11. The biopsy device of claim 9, wherein the device further comprises a source of fluid or air attached to the hub of the semi-circular tube.

12. The biopsy device of anyone of claims 4–11, wherein the device further comprises a hollow cannula, and a source of negative pressure attached to the cannula.

13. A method of removing tissue from the body of an animal with a device including an elongated hollow outer tube having a first end, a second, open end, and an opening having at least one sharpened cutting edge, and the device including an inner tube having a first end and a second end capable of penetrating tissue, the method comprising the steps of:

(a) inserting the inner tube in the outer tube with the second end of the inner tube extend out of the second end of the outer tube;

(b) inserting the inner and outer tubes together into the body of the animal to the location of the tissue to be removed;

(c) removing the inner tube from the outer tube;

(d) collecting the tissue to be removed in the opening in the outer tube;

(e) moving the outer tube so that the at least one cutting edge severs the tissue collected within the opening; and (f) removing the outer tube with the tissue positioned therein.

14. The method of claim 13, wherein the method further comprises applying negative pressure to the outer tube.

15. The method of claim 13, wherein the method further comprises:

providing a sealed container, a first flexible tube having two ends, and a second flexible tube having two ends, wherein one end of the first flexible tube is connected to the first end of the hollow outer tube and the other end of the first tube is connected to the container, and wherein one end of the second flexible tube is connected to the container;

applying a negative pressure to the second flexible tube.

16. The method of claim 13, wherein the method further comprises: providing an elongated hollow inner semi-circular tube having a flat base, a radius that is less than half of the diameter of the hollow outer tube, and when inserted into the hollow outer tube creates two lumens; wherein the first lumen is defined by the space between the flat base and the inner surface of the outer hollow tube; and wherein the second lumen is defined by the space inside the inner semi-circular tube; and wherein the flat base has holes along its surface in an area under the rectangular opening, to permit the first lumen to communicate with the second lumen.

17. The method of claim 16, wherein the method further comprises applying negative pressure to the first lumen;

injecting fluid or air through the second lumen;

collecting tissue with fluid or air emerging from the first lumen in a container.

18. The method of claim 17, wherein the step of applying negative pressure to the first lumen comprises providing a hollow cannula, and a source of negative pressure attached to the cannula;

inserting the hollow cannula into the first lumen and advancing the cannula at least as far as the rectangular opening; and applying negative pressure.

19. The method of claim 16, wherein the method further comprises applying negative pressure to the first lumen;

applying negative pressure to the second lumen;

collecting tissue emerging from the first lumen in a container.

20. The method of claim 19, wherein the method further comprises providing a hollow cannula, and a source of negative pressure attached to the cannula;

inserting the hollow cannula into the first lumen and advancing the cannula at least as far as the rectangular opening; and applying negative pressure.

21. A biopsy device for removing tissue from the body of an animal, the device comprising:

an elongated hollow outer tube having a first end, a second end, and a longitudinal axis, the second end being open, the tube including an opening formed therein spaced back from the second end, the opening having at least one sharpened cutting edge; and a stylus having a first end and a second end and a longitudinal axis, the second end having a shape capable of piercing tissue, the stylus capable of fitting inside the hollow tube with the second end of the stylus protruding from the second end of the outer tube to allow positioning of the outer tube at a site of the tissue to be removed.

22. The biopsy device of claim 21, wherein the device further comprises a source of negative pressure attached to the first end of the hollow outer tube.

23. The biopsy device of claim 22, wherein the source of negative pressure comprises a sealed container, a first flexible tube having two ends, and a second flexible tube having two ends, wherein one end of the first flexible tube is connected to the first end of the hollow outer tube and the other end of the first tube is connected to the container, and wherein one end of the second flexible tube is connected to the container and the other end is connected to a device that draws air from the container.

24. The biopsy device of claim 21, wherein the outer tube further comprises an elongated member positioned within the hollow outer tube substantially parallel to its longitudinal axis, so as to separate the tube into a first lumen and a second lumen.

25. The biopsy device of claim 24, wherein the device further comprises a source of negative pressure attached to the second lumen at its first end.

26. The biopsy device of claim 25, wherein the source of negative pressure comprises a sealed container, a first flexible tube having two ends, and a second flexible tube having two ends, wherein one end of the first flexible tube is connected to the first end of the hollow outer tube and the other end of the first tube is connected to the container, and wherein one end of the second flexible tube is connected to the container and the other end is connected to a device that draws air from the container.

27. The biopsy device of claim 1, wherein the device further comprises an elongated hollow inner semi-circular tube having a flat base, a radius that is at all points along the tube less than half of the diameter of the hollow outer tube, and when inserted into the hollow outer tube creates two lumens;

wherein the first lumen is defined by the space between the flat base and the inner surface of the outer hollow tube; and wherein the second lumen is defined by the space inside the inner semi-circular tube; and wherein the flat base has holes along its surface in an area under the rectangular opening, to permit the first lumen to communicate with the second lumen.

28. The biopsy device of claim 27, wherein the hollow inner semi-circular tube further comprises a hub attached to the first end of the semi-circular tube.

29. The biopsy device of claim 28, wherein the device further comprises a source of negative pressure attached to the hub of the semi-circular tube.

30. The biopsy device of claim 28, wherein the source of negative pressure comprises a sealed container, a first flexible tube having two ends, and a second flexible tube having two ends, wherein one end of the first flexible tube is connected to the first end of the hollow outer tube and the other end of the first tube is connected to the container, and wherein one end of the second flexible tube is connected to the container and the other end is connected to a device that draws air from the container.

31. The biopsy device of claim 28, wherein the device further comprises a source of fluid or air_attached to the hub of the semi-circular tube.

32. The biopsy device of anyone of claims 24–31, wherein the device further comprises a hollow cannula, and a source of negative pressure attached to the cannula.

33. A biopsy device for removing tissue from the body of an animal, the device comprising:
- an elongated hollow outer tube comprising a first end, a second end, and a longitudinal axis, wherein the outer tube has a total length of about 40 mm–250 mm and a diameter of a 11–22 gauge needle;
- two substantially parallel longer edges and one substantially parallel shorter edges defining a triangular opening about 0.5 mm–20 mm from the second end of the outer tube, wherein the longer edges are positioned within 25–75° from the longitudinal axis of the outer tube, have a length of about 5 mm–30 mm, and are sharpened to a cutting edge, and wherein the shorter edge has a length equal to about 15–50% of the diameter of the hollow outer tube, and wherein the shorter edge closer to the second end of the tube is sharpened to a cutting edge; and
- a hub attached at the first end of the hollow outer tube.

34. A biopsy device for removing tissue from the body of an animal, the device comprising:
- an elongated hollow outer tube comprising a first end, a second end, and a center axis, wherein the outer tube has a total length of about 40 mm–250 mm and a diameter of a 11–22 gauge needle;
- an elongated sharpened cutting edge defining an elliptical opening having two foci lying along the central axis; wherein one focus is about 0.5 mm–20 mm from the second end of the outer tube and the other focus is at least 5 mm further, and wherein the sum of the distance between one focus and a point on the edge, and the other focus and the point, is equal to about 50–150% of the diameter of the tube;
- a hub attached at the first end of the hollow outer tube.

35. The method of claim 13, further comprising the step (g) of reinserting the inner tube into the outer tube to remove the tissue from the outer tube after removing the outer tube from the body in the step (f).

36. The method of claim 13, the step (d) of collecting the tissue in the opening comprising the step of applying a negative pressure to draw the tissue into the space vacated by the inner tube.

37. The method of claim 13, the step (e) of moving the outer tube comprises rotating the outer tube to sever the tissue.

38. The method of claim 13, the step (e) of moving the outer tube comprises translating the outer tube along a longitudinal axis of the outer tube to sever the tissue.

39. The method of claim 13, the step (b) of inserting the inner and outer tubes into the body comprising the steps of:
- inserting a trocar into the body to a point where an end of the trocar is positioned adjacent the site of the tissue to be removed; and
- inserting the inner and outer tubes through the trocar until the second ends of the inner and outer tube extend from the end of the trocar.

40. The biopsy device of claim 21, the opening formed by two substantially parallel longer edges and two substantially parallel shorter edges defining a rectangular opening.

41. The biopsy device of claim 40, to form the at least one sharpened cutting edge.

42. The biopsy device of claim 40, the shorter edge nearest the second end being sharpened to form the at least one sharpened cutting edge.

43. The biopsy device of claim 40, the two longer edges being sharpened and the shorter edge nearest the second end being sharpened to form the at least one sharpened cutting edge.

* * * * *